(12) United States Patent (10) Patent No.: US 8,684,935 B2
Humayun et al. (45) Date of Patent: Apr. 1, 2014

(54) INTRAOCULAR ULTRASOUND DOPPLER TECHNIQUES

(75) Inventors: Mark S. Humayun, Glendale, CA (US); Xiaochen Xu, Los Angeles, CA (US); Qifa Zhou, Arcadia, CA (US); K. Kirk Shung, Monterey Park, CA (US); Hossein Ameri, Alhambra, CA (US); Gerald Chader, Pasadena, CA (US)

(73) Assignee: Doheny Eye Institute, Los Angeles, CA (US)

( * ) Notice: Subject to any disclaimer, the term of this patent is extended or adjusted under 35 U.S.C. 154(b) by 1083 days.

(21) Appl. No.: 12/102,293

(22) Filed: Apr. 14, 2008

(65) Prior Publication Data

US 2008/0319319 A1 Dec. 25, 2008

Related U.S. Application Data

(63) Continuation-in-part of application No. 12/061,147, filed on Apr. 2, 2008, and a continuation-in-part of application No. 12/061,120, filed on Apr. 2, 2008.

(60) Provisional application No. 60/911,385, filed on Apr. 12, 2007.

(51) Int. Cl.
*A61B 8/14* (2006.01)

(52) U.S. Cl.
USPC .......................... 600/459; 600/454; 600/462

(58) Field of Classification Search
USPC .................................. 600/437–469, 473–480
See application file for complete search history.

(56) References Cited

U.S. PATENT DOCUMENTS

| 3,556,079 | A | * | 1/1971 | Omizo | 600/461 |
|---|---|---|---|---|---|
| 4,671,292 | A | * | 6/1987 | Matzuk | 600/445 |
| 4,887,606 | A | * | 12/1989 | Yock et al. | 600/461 |
| 5,119,821 | A | * | 6/1992 | Tuchler | 600/454 |
| 5,131,394 | A | * | 7/1992 | Gehlbach | 600/461 |
| 5,131,395 | A | * | 7/1992 | Gehlbach | 600/461 |
| 5,311,871 | A | * | 5/1994 | Yock | 600/461 |
| 5,421,336 | A | * | 6/1995 | De Bernardis | 600/461 |
| 5,570,692 | A | * | 11/1996 | Morinaga | 600/453 |
| 5,931,784 | A | | 8/1999 | Kajiwara et al. | |
| 5,979,453 | A | * | 11/1999 | Savage et al. | 128/898 |

(Continued)

FOREIGN PATENT DOCUMENTS

| JP | 2002518122 | 6/2002 |
|---|---|---|
| KR | 1999014883 | 2/1999 |
| KR | 20030024597 | 3/2003 |

OTHER PUBLICATIONS

International Search Report for corresponding PCT Application No. PCT/US2008/060212, 3 pp.

(Continued)

*Primary Examiner* — Sanjay Cattungal
(74) *Attorney, Agent, or Firm* — McDermott Will & Emery LLP

(57) ABSTRACT

Systems and methods are disclosed providing for the use of ultrasound energy to measure blood flow within blood vessels by Doppler velocity measurement. Directional high-frequency pulsed-wave Doppler measurements can be made with a suitable ultrasonic needle transducers for in vivo measuring of blood flow. A needle probe can include a ultrasonic material such as PMN-PT. Such blood flow measurements can be made in any part of the body, e.g., in the central retinal vein and branch retinal veins.

23 Claims, 4 Drawing Sheets

(56) References Cited

U.S. PATENT DOCUMENTS

| | | | |
|---|---|---|---|
| 6,004,269 A * | 12/1999 | Crowley et al. | 600/439 |
| 6,048,312 A * | 4/2000 | Ishrak et al. | 600/443 |
| 6,554,770 B1 | 4/2003 | Sumanaweera et al. | |
| 6,565,513 B1 | 5/2003 | Phillips | |
| 6,669,642 B2 | 12/2003 | Amemiya et al. | |
| 2008/0091104 A1 * | 4/2008 | Abraham | 600/439 |
| 2009/0036772 A1 * | 2/2009 | Lu | 600/437 |
| 2009/0118612 A1 * | 5/2009 | Grunwald et al. | 600/424 |
| 2010/0152625 A1 * | 6/2010 | Milo | 601/2 |

OTHER PUBLICATIONS

Written Opinion for corresponding PCT Application No. PCT/US2008/060212, 3 pp.

* cited by examiner

INTRAOCULAR ULTRASOUND DOPPLER TECHNIQUES

RELATED APPLICATIONS

This application is a continuation-in-part of related U.S. patent application Ser. No. 12/061,147 filed 2 Apr. 2008 and entitled "Preoperative and Intra-Operative Lens Hardness Measurement by Ultrasound," which claims the benefit of U.S. Provisional Patent Application No. 60/909,496 filed 2 Apr. 2007; this application also is a continuation-in-part of U.S. patent application Ser. No. 12/061,120 filed 2 Apr. 2008 and entitled "Thrombolysis In Retinal Vessels with Ultrasound," which claims the benefit of U.S. Provisional Patent Application No. 60/911,385 filed 12 Apr. 2007; this application claims the benefit of U.S. Provisional Patent Application No. 60/911,385 filed 12 Apr. 2007 and U.S. Provisional Patent Application No. 61/030,075 filed 20 Feb. 2008; the entire contents of all of which applications are incorporated herein by reference.

BACKGROUND

Several procedures have been devised to surgically remove the obstruction and reestablish the blood flow. During these surgeries quantitative analysis is typically needed to evaluate blood flow. Currently, two evaluation methods are commonly used: fluorescein angiography and ultrasound color Doppler:

Fluorescein angiography in which fundus photos are taken after injecting the fluorescein dye into an arm vein is commonly used for both diagnosing retinal vein occlusion and evaluating treatments of retinal vein occlusion. Due to the medial opacities, fluorescein angiography is inadequate for both diagnosing and evaluating central retinal vein occlusion. Furthermore, in the fluorescein angiography procedure, multiple photos are taken by a camera with special filters, and they are analyzed subjectively by ophthalmologists. This method may not be suitable for instantaneously evaluating blood flow reestablishment during surgeries.

Some researchers have demonstrated the feasibility of measuring the blood flow velocities from the central retinal vein and artery behind the optic disc, using commercial color Doppler systems. These studies have shown a significant reduction in flow velocity in the central retinal vein in situations of central retinal vein occlusion ("CRVO"). These velocity variances may be used to diagnose CRVO. Ultrasound color Doppler techniques have typically operated at frequencies of less than 15 MHz. The corresponding achievable velocity resolutions of 1~2 cm/s are insufficient for both the accurate clinical diagnosis and treatment evaluation, and the bulky ultrasound probe size introduces some setup complexities for the instantaneous flow evaluation during surgery. This method may not be suitable during an ophthalmologic surgery either.

A pulsed-wave Doppler system with a PMN-PT needle transducer has been developed to measure the blood flow velocity in selected retinal vessels. See, e.g., Emanuel J. Gottlieb, et al., "PMN-PT High Frequency Ultrasonic Needle Transducers for Pulsed Wave Doppler In The Eye," 2005 IEEE Ultrasonics Symposium (IEEE 2005), the contents of which are incorporated herein by reference in their entirety.

Ultrasonic techniques have also been utilized in surgical procedures on the eye for imaging structure and/or tissue of a surgical site. See, e.g., U.S. Pat. No. 6,676,607 to de Juan, Jr. et al., the contents of which are incorporated herein by reference in their entirety.

While prior art techniques have proven useful for their respective intended purposes, they can present difficulties or limitations with respect to thrombolysis in retinal eye vessels. Such drawbacks have included the unwanted side effects on human tissue from high power intensities.

SUMMARY

The present disclosures provides methods, techniques, systems, and apparatus utilizing directional high-frequency pulsed-wave Doppler measurements, e.g., with a suitable ultrasonic needle transducers (e.g., one made of PMN-PT), for in vivo measuring of blood flow. Such blood flow measurements can be made in any part of the body, e.g., in the central retinal vein and branch retinal veins. Such techniques/technology can present one or more of the following advantages, compared to the current evaluation methods mentioned above.

Improved Velocity Resolution of the Measurement(s).

Better velocity resolution and lower minimal detectable velocity cab be realized owing to the use of high-frequency ultrasound (e.g., >40 MHz). Such use can provide for detection of velocities as low as 0.1 mm/s and can provide a velocity resolution of 0.005 mm/s.

Easier Use.

Embodiments of the present disclosure can be easily used/operated by ophthalmologists. A whole system can be compact, and ultrasonic needle transducers and probes according to the present disclosure can be similar in size and shape to the microsurgical instruments used in an ophthalmologic surgery.

Lower Cost.

The total cost of systems of the present disclosure, which can be reusable, can be relatively low, e.g., less than $2000.

Other features and advantages of the present disclosure will be understood upon reading and understanding the detailed description of exemplary embodiments, described herein, in conjunction with reference to the drawings.

BRIEF DESCRIPTION OF DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings.

Figure 1:
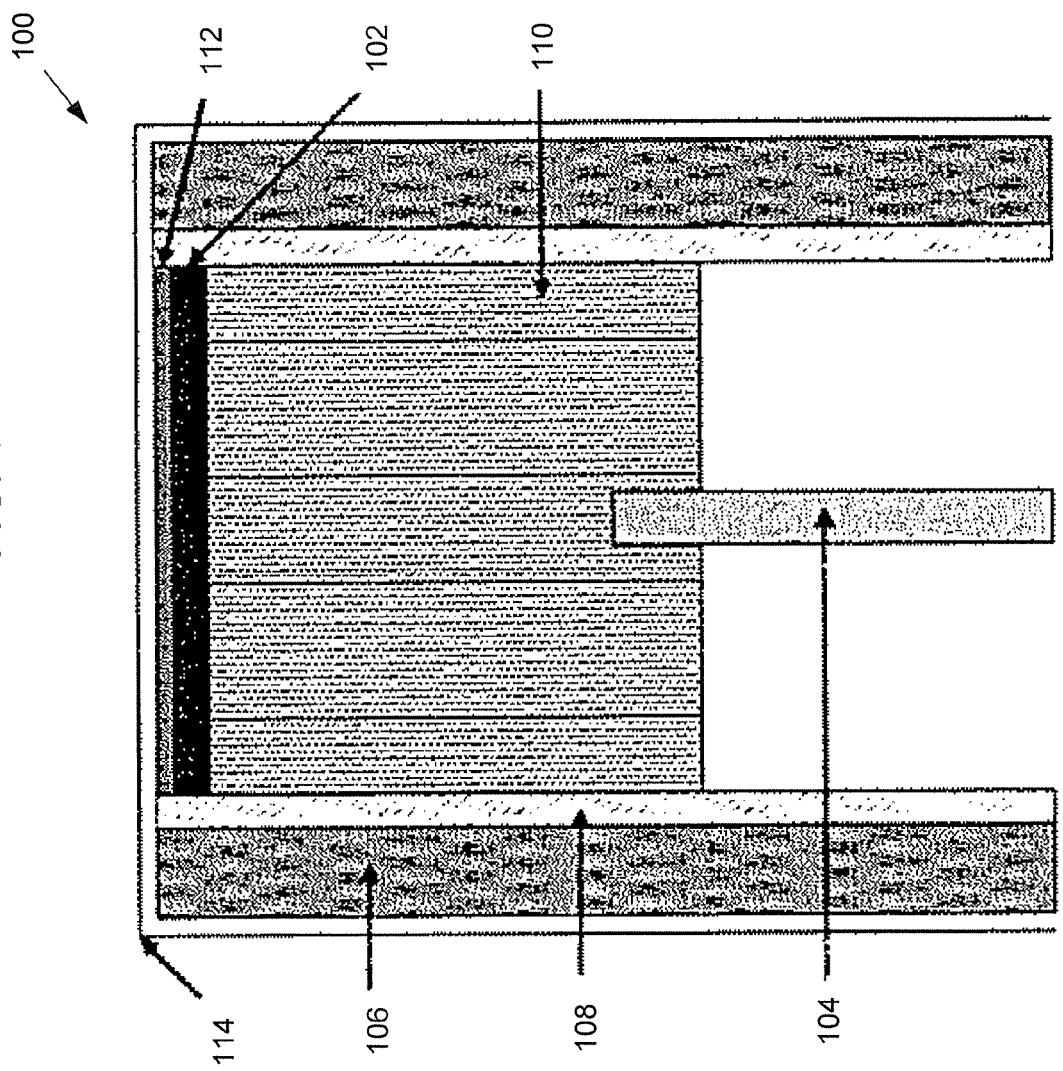
FIG. 1 depicts a design cross section of a suitable PMN-PT needle transducer for blood flow measurement, in accordance with an embodiment of the present disclosure.

One skilled in the art will appreciate that the embodiments depicted in the drawings are illustrative and that variations of those shown, as well as other embodiments described herein, may be envisioned and practiced within the scope of the present disclosure.

DETAILED DESCRIPTION

Embodiments of the present disclosure are directed to a pulsed-wave Doppler system including an ultrasonic needle transducer to measure the blood flow velocity in selected retinal vessels. The transducer can include a suitable active piezoelectric material. In exemplary embodiments, a suitable piezoelectric material can include lead magnesium niobate lead titanate (e.g., PMN-33% PT) though other suitable piezoelectric transducer materials may be substituted or added.

Ultrasonic transducers or needle probes as disclosed herein can be combined with or coupled to various endoscopes used throughout body cavities, e.g., as used to evaluate tumors such as melanoma, etc. Ultrasonic transducers or needle probes according to the present disclosure may also be combined within, coupled to, or otherwise employed with various suitable surgical instruments and/or components of surgical instruments and/or surgical systems. For example, a needle probe (with ultrasonic transducer) can be coupled to cryogenic (cryo), laser, illumination, and/or cautery probes used for various parts of the body, including internal body cavities. Further examples of surgical components/instruments to which needle probes can be coupled include, but are not limited to, one or more light fibers and/or optical coherence tomography probes, and the like.

High frequency ("HF") ultrasound Doppler can be used to detect blood flow in the microcirculation. In HF ultrasound applications, the large tissue attenuation at high frequency limits the penetration depth of acoustic wave. Therefore, to facilitate blood flow measurement at a targeted or desired region of a patient's body, e.g., behind the optic disc which is located about 2 cm away from the cornea, an HF intraocular transducer can be inserted into the patient in an appropriate procedure. For example, to measure the blood flow behind the optic disc an ultrasonic probe (also referred to as an HF transducer) can be inserted through the sclera or inserted around the eye (i.e., in the orbit); such insertion procedures can be performed in the same or a similar way as for other microsurgical instruments used in surgery.

Exemplary embodiments of the present disclosure can include a needle probe with a piezoelectric (e.g., PMN-PT) transducer configured at a desired angle with respect to the longitudinal axis of the probe. For example, exemplary embodiments with 0° and 45° tips have been fabricated and tested successfully. In vivo studies have been carried out on rabbits. The system can measure the flow velocities from blood vessels. In exemplary embodiments, the blood vessels can be retinal vessels, including the central retinal vein and artery, and the branch retinal veins and arteries. The measurement error of this system can be less than 10% in exemplary embodiments.

Figure 2:
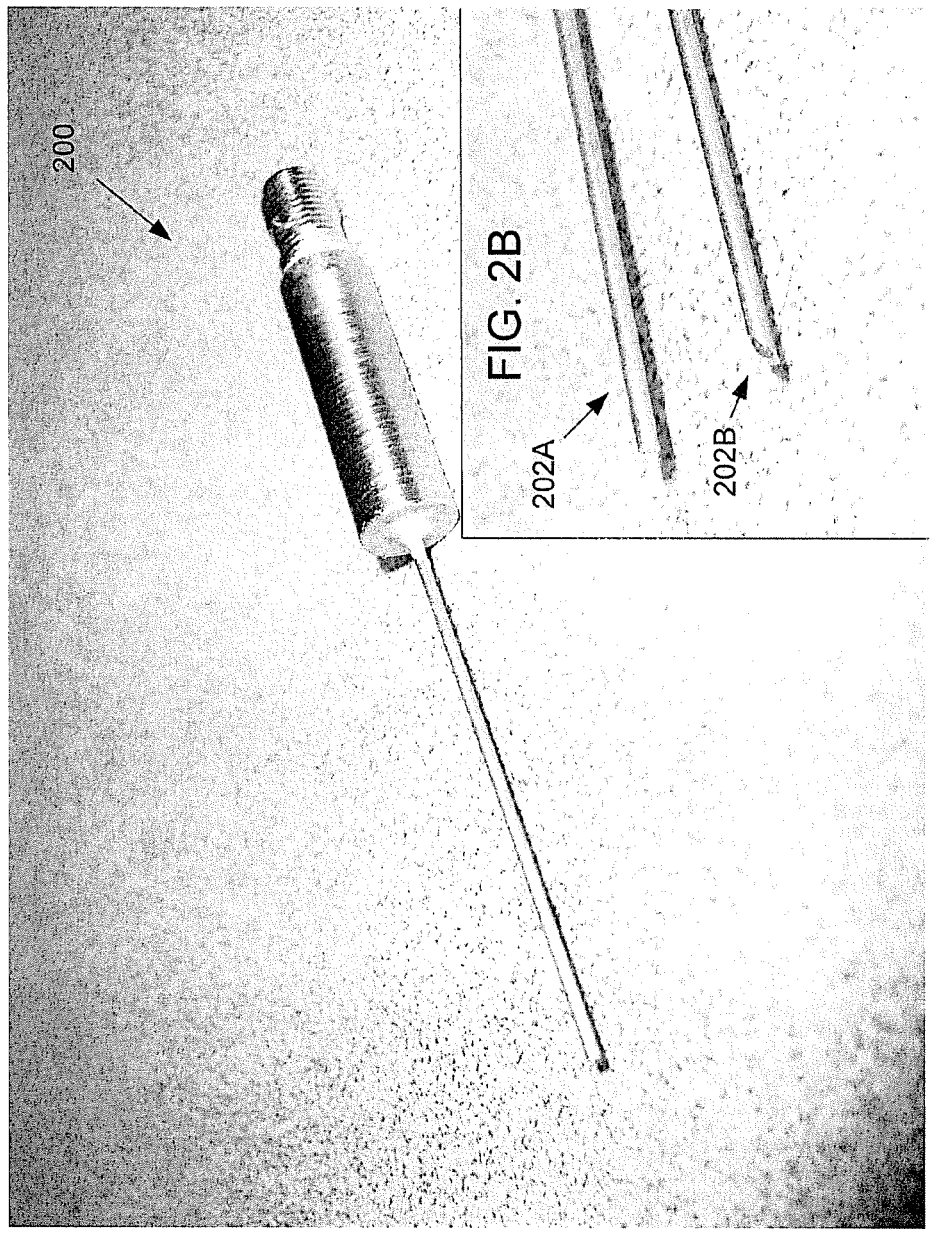
FIG. 2A is a perspective view of a PMN-PT needle transducer in accordance with an exemplary embodiment of the present disclosure.
FIG. 2B includes a perspective view of embodiments of needle transducers in accordance with the present disclosure.

FIG. 1 and FIG. 2 depict a PMN-PT needle transducer with diameter of 0.9 mm, according to an exemplary embodiment. The embodiments depicted, e.g., transducers with 0° and 45° tips, can be used to measure blood flow, e.g., from the central retinal vessels behind the optic disc, and blood flow from the branch retinal vessels on the retina. The PMN-PT needle probe has the advantages of high sensitivity, affordable price, and simple fabrication procedures. The measured lateral resolution of the probe at 2 mm, which is the typical distance from the probe to the vessels during measurements, was about 300 µm.

FIG. 1 depicts a design cross section of a suitable PMN-PT needle transducer for retinal blood flow measurement with Doppler techniques, in accordance with an embodiment of the present disclosure.

As shown in FIG. 1, the probe 100 can include a piezoelectric material 102 disposed with a needle housing 106. The piezoelectric material 102 can be any suitable active piezoelectric material. One suitable piezoelectric material is lead magnesium niobate lead titanate (e.g., PMN-33% PT). The piezoelectric material may be attached (directly or indirectly, and with suitable electrical configuration/connection) to an electrical connector 104 by suitable fabrication/construction techniques. For example, Cr/Au electrodes can be used to connect the piezoelectric material 102 to the electrical connector 104, though other conductive material(s) may be used. Housing 106 can be of a desired diameter and material, e.g., steel of 1 mm diameter, which size can be suitable (or selected) for insertion into an ocular incision. The needle housing 106 can surround a tube 108 of electrically insulating/isolating material, e.g., made of polyimide fabricated by suitable techniques. The electrical connector may be one suitable for connection to a control system configured to control the production of acoustic energy from the transducer, for example system 300 show and described for FIG. 3 herein.

Continuing with the description of probe 100, a conductive backing material 110 can be located between the piezoelectric material 102 and the electrical connector 104. A matching layer 112 may be located on or adjacent to the side of the probe from which acoustic energy is to be produced. A protective coating 114 may optionally be present, with parylene being an exemplary material for the protective coating, though others may be used.

FIG. 2A is a perspective view of an exemplary PMN-PT needle transducer 200. FIG. 2B is an inset showing embodiments of the needle transducer tip having either a 0° or 45° tip (202A, 202B) in accordance with an embodiments of a system according to the present disclosure. Other angles may be used for the tip configuration.

For the exemplary embodiment of needle transducer 200 in FIG. 2A, a 700 µm thick PMN-PT (HC Material Corp., Urbana, Ill.) was lapped to 51 µm. A matching layer made of Insulcast 501 and Insulcure 9 (American Safety Technologies, Roseland, N.J.) and 2-3 µm silver particles (Sigma-Aldrich Inc., St. Louis, Mo.) was cured over the PMN-PT and lapped to 10 µm. A conductive backing material, E-solder 3022 (VonRoll Isola, New Haven, Conn.), was cured over the opposite side of the PMN-PT and lapped to under 3 mm. Active element plugs were diced out at 0.4 mm aperture (0.4 mm×0.4 mm) and housed using Epotek 301 (Epoxy Technology Inc., Billerica, Mass.) within a polyimide tube with inner diameter of 0.57 mm (MedSource Technologies, Trenton, Ga.). An electrical connector was fixed to the conductive backing using a conductive epoxy. The polyimide tube provided electrical isolation from the 20 gage needle housing with inner diameter 0.66 mm. An electrode was sputtered across the silver matching layer and the needle housing to form the ground plane connection. Vapor deposited parylene with thickness of 13 µm was used to coat the aperture and the needle housing.

As described previously, a suitable electronic system can be used to control/excite a needle probe (e.g., probe 200 of FIG. 2A) used for ultrasound-based thrombolysis according to the present disclosure. An example of such a system is shown in FIG. 3.

Figure 3:
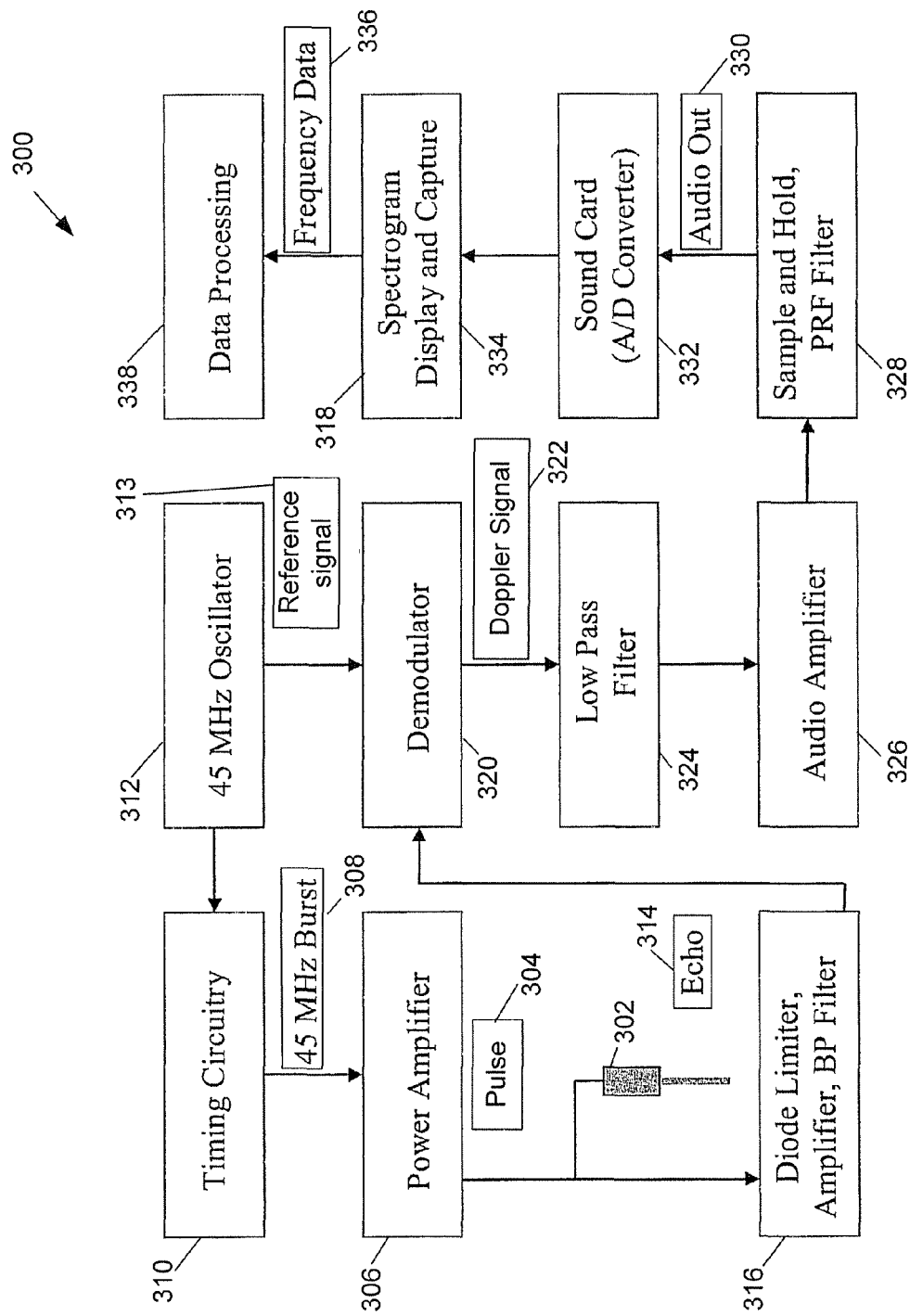
FIG. 3 is a box diagram representing a control system in accordance with an embodiment of the present disclosure.

FIG. 3 is a box diagram representing an exemplary system 300 (or controller) for controlling a needle probe (e.g., a PMN-PT needle probe described for FIGS. 1-2), in accordance with an embodiment of the present disclosure. System 300 can include both (i) excitation components for controlling the ultrasonic output of a transducer, e.g., needle probes 100 and 200 of FIGS. 1-2, and also (ii) optional circuitry/components for Doppler detection of blood flow in retinal blood vessels.

As shown in FIG. 3, system 300 can include a piezoelectric transducer or probe 302. Probe 302 can be connected to, or operation to receive signals/pulses from a pulse generation block, which can include a power amplifier 306, timing circuitry 310, and a suitable clock or oscillator 312, e.g., a 45 MHz clock generator (or oscillator). System 300 can operate as a pulser, e.g., a N-cycle bipolar pulser, to generate one or more suitable pulses for supplying the transducer 302 with electrical energy for conversion to acoustic ultrasound energy. In exemplary embodiments, system 300 can produce a N-cycle bi-polar pulse with 70 Vpp, for the control of the associated ultrasonic probe/transducer 302. The pulse repetition frequency (PRF) of the produced pulse(s) produced by system 300 can be adjusted as desired, e.g., from 100 Hz to 100 KHz, and the cycle count of the pulse can be adjusted as desired, e.g., from 1 to 255. Both the PRF and cycle count can correspond to different acoustic intensities, e.g., different flow velocities created by the acoustic streaming or the actual measured velocities.

In exemplary embodiments, the system 300 can include a clock generator operating at a desired frequency, e.g., 45-46 MHz, timing circuits, and a N-cycle bipolar pulser. Using the system, a N-cycle bi-polar pulse with 20~70 Vpp can be generated. The pulse repetition frequency (PRF) of pulse can be adjusted from 100 Hz to 100 KHz, and the cycle count of the pulse can be adjusted from 1 to 255. The pulses can be used to excite the transducers. The received echoes from the needle transducer are preferably limited and then amplified, e.g., by Miteq-1114. The amplified signals can be first band-pass filtered by a 45 MHz custom band-pass filter and then fed to the in-phase and quadrature demodulator. The demodulated intermediate frequency (IF) signals can be low-pass filtered to remove harmonics and noise by low-pass filters. Then the signals can be sampled and held. Followed by the PRF filters, the sampled-and-held signals can be cleaned by removing sample-and-hold harmonics. Also the optional wall filters can be followed to remove low-frequency clutter signals. Finally, the amplified Doppler signals can be played by the stereo speakers and digitized by a sound card. The digitized Doppler signals can be converted into a directional spectrogram, e.g., by Labview software in real time. Further off-line analysis can be conducted, e.g., using MatLab based software. In an exemplary embodiment, a micro flow phantom consisting of 127~574 μm tubes was set up and was used to evaluate the system.

Figure 4:
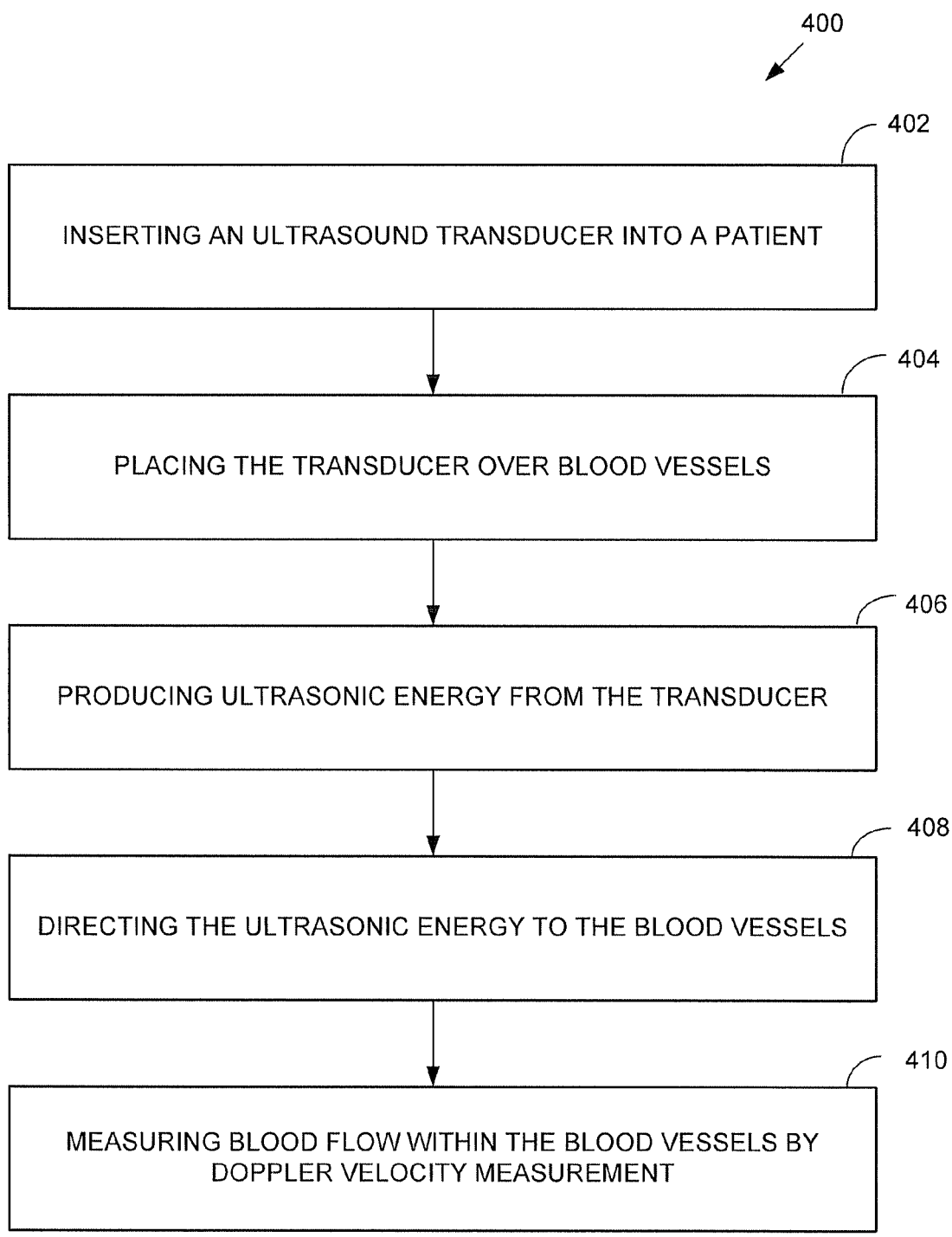
FIG. 4 depicts a method of in vivo measurement of blood flow in retinal blood vessels according to an exemplary embodiment of the present disclosure.

FIG. 4 depicts a method 400 of measuring blood flow in a blood vessel according to an exemplary embodiment of the present disclosure. The blood vessels can be anywhere in a patient's body, e.g., the eye, heart, leg, etc. An ultrasound transducer can be inserted into a patient, as described at 402. The transducer may be place over targeted blood vessels, as described at 404. The targeted blood vessels may include one or more blood clots. Ultrasonic energy can be produced from the transducer of a probe, e.g., probe 200A of FIG. 2B, as described at 406. For example, an electronic control system according (or similar) to FIG. 3 can be used to control the production, e.g., 406, or ultrasonic energy.

Continuing with the description of method 400, the ultrasonic energy can be directed to the targeted, e.g., retinal, vessels, as described at 408. Directing ultrasonic energy can include producing acoustic streaming in the blood of the targeted blood vessels. As described at 410, measurement of blood flow (e.g., velocity and/or flow rate) in the targeted blood vessels can accordingly be effected.

Accordingly, compared to the existing technologies, embodiments of the present disclosure can provide the advantage of better velocity resolution and lower minimal detectable velocity. Because we are using the high-frequency ultrasound (>45 MHz), the proposed method can detect velocities as low as 0.1 mm/s and has a velocity resolution of 0.005 mm/s. Techniques and apparatus of the present disclosure can be much easier to use than prior art techniques. Systems according to the present disclosure can be compact and needle probes with a piezoelectric (e.g., PMN-PT) transducer can be similar in size and shape to the microsurgical instruments used in an ophthalmologic surgery. Systems of the present disclosure, which can be disposable, can be relatively inexpensive.

Moreover, a needle probe according to the present disclosure, such as depicted in FIGS. 1-2, can provide the advantages of high efficiency, affordable price, and simple fabrication procedures. Such a probe can have a (natural) focal point at a desired distance from the tip of the prove, e.g., at approximately 1~2 mm. For an exemplary embodiment, a PMN-NT probe according to FIGS. 1-2 had a measured lateral resolution of about 300 μm at a distance of 2 mm. Such lateral resolution and focal distance parameters can be particularly useful for clot dislodging as a typical central retinal vein locates at 1 mm below the optical nerve.

While certain embodiments have been described herein, it will be understood by one skilled in the art that the methods, systems, and apparatus of the present disclosure may be embodied in other specific forms without departing from the spirit thereof. For example, while certain piezoelectric materials have been mentioned specifically, others may be used within the scope of the present disclosure.

Accordingly, the embodiments described herein are to be considered in all respects as illustrative of the present disclosure and not restrictive.

What is claimed:

1. A system comprising:
   an ultrasound probe including an ultrasonic transducer configured to produce an output of ultrasound energy, wherein the ultrasonic transducer comprises a piezoelectric material including PMN-PT, the probe being configured for insertion in an eye of a patient, wherein the ultrasonic energy is produced at a frequency of about 45 MHz to about 50 MHz;
   a control unit connected to the ultrasound transducer and configured to control the production of ultrasound energy from the transducer; and
   a measurement unit configured to measure blood flow within blood vessels by Doppler velocity measurement, wherein the measurement unit is configured to detect blood flow velocities of about 0.1 mm/s with a velocity resolution of about 0.005 mm/s.

2. The system of claim 1, wherein the ultrasound transducer comprises a flat, angled or beveled tip.

3. The system of claim 1, wherein the ultrasound transducer includes a cylindrical housing.

4. The system of claim 3, wherein the cylindrical housing comprises steel.

5. The system of claim 4, wherein the steel comprises stainless steel.

6. The system of claim 3, further comprising a flexible tube disposed within the cylindrical housing.

7. The system of claim 6, wherein the flexible tube comprises polyimide.

8. The system of claim 1, wherein the PMN-PT comprises PMN-33% PT.

9. The system of claim 1, wherein the control unit comprises timing circuitry and a power amplifier.

10. The system of claim 1, wherein the control unit is configured and arranged to control the intensity of the output.

11. The system of claim 1, wherein the control unit is configured and arranged to control the pulse repetition frequency (PRF) of the output.

12. The system of claim 1, wherein the controller is configured and arranged to produce a pulse repetition frequency of about 100 Hz to about 100 kHz.

13. The system of claim 1, wherein the controller is configured ad arranged to produce a pulse cycle count from 1 to 255.

14. A method of measuring blood flow in a blood vessel, the method comprising:
 inserting a needle probe with an ultrasonic transducer into an eye of a patient, wherein the ultrasonic transducer comprises a piezoelectric material including PMN-PT;
 placing the transducer over blood vessels in the patient's eye;
 producing ultrasonic energy from the transducer, wherein the ultrasonic energy is produced at a frequency of about 45 MHz to about 50 MHz;
 directing the ultrasonic energy to the blood vessels; and
 with a measurement unit configured to measure blood flow within blood vessels by Doppler velocity measurement, measuring blood flow within blood vessels by Doppler velocity measurement, wherein the measurement unit is configured to detect blood flow velocities of about 0.1 mm/s with a velocity resolution of about 0.005 mm/s.

15. The method of claim 14, wherein measuring blood flow within blood vessels includes measuring blood velocity.

16. The method of claim 14, further comprising measuring volumetric flow rate.

17. The method of claim 14, further comprising coupling the needle probe to a surgical instrument or component.

18. The method of claim 17, wherein the surgical instrument or component comprises an endoscope, a laser probe, a cryoprobe, a light fiber, and/or an optical coherence tomography probe.

19. The method of claim 14, further comprising receiving ultrasonic energy reflected from the targeted blood vessels.

20. The method of claim 14, wherein producing ultrasonic energy from the transducer comprises producing a pulse repetition frequency of about 100 Hz to about 100 kHz.

21. The method of claim 14, wherein producing ultrasonic energy from the transducer comprises producing a pulse cycle count from 1 to 255.

22. The method of claim 14, wherein producing ultrasonic energy from the transducer comprises using a piezoelectric needle probe.

23. The method of claim 14, wherein placing the transducer over blood vessels in the patient's eye comprises placing the transducer over or adjacent to retinal vessels of the eye or the optic nerve of the patient.

* * * * *